United States Patent [19]

Wenger

[11] Patent Number: 4,764,503
[45] Date of Patent: Aug. 16, 1988

[54] NOVEL CYCLOSPORINS

[75] Inventor: Roland Wenger, Riehen, Switzerland

[73] Assignee: Sandoz Ltd., Basel, Switzerland

[21] Appl. No.: 49,746

[22] Filed: May 13, 1987

Related U.S. Application Data

[63] Continuation of Ser. No. 932,760, Nov. 19, 1986, abandoned, which is a continuation of Ser. No. 713,259, Mar. 19, 1985, abandoned.

[51] Int. Cl.$^4$ .................. A61K 37/02; C07K 5/12
[52] U.S. Cl. .................... 514/11; 530/317
[58] Field of Search ................. 530/321; 514/11

[56] References Cited

U.S. PATENT DOCUMENTS 4,108,985  8/1978  Ruegger et al. ............... 514/11
4,210,581  7/1980  Ruegger et al. ............... 530/321
4,220,641  9/1980  Traber et al. ................. 514/11

*Primary Examiner*—Delbert R. Phillips
*Attorney, Agent, or Firm*—Gerald D. Sharkin; Robert S. Honor; Thomas O. McGovern

[57] ABSTRACT

Cyclosporins wherein the amino acid residue at the 8-position is a (D)-acyloxy-α-amino acid residue, typically of formula ┌─X-Y-Sar-MeLeu-Z-MeLeu-Ala-Q-MeLeu-MeLeu-MeVal─┐ wherein X=—MeBmt— or —dihydro—MeBmt—, Y=—αAbu—, —Ala—, —Thr—, —Val— or —Nva—, Z=—Val— or —Nva— and Q=$R_1$—CO—O—CH($R_2$)—CH(CO—)—NH— wherein $R_1$=H, $C_{1-4}$alkyl or phenyl and $R_2$=H or $CH_3$, possess immunosuppressive, anti-inflammatory and anti-parasitic activity.

6 Claims, No Drawings

NOVEL CYCLOSPORINS

This is a continuation of application Ser. No. 932,760, filed Nov. 19, 1986, which in turn is a continuation of application Ser. No. 713,259, filed Mar. 19, 1985, both now abandoned.

The present invention relates to novel cyclosporins, processes for their production, their use as pharmaceuticals and pharmaceutical compositions comprising them.

The cyclosporins comprise a class of structurally distinctive, cyclic, poly-N-methylated undecapeptides commonly possessing pharmacological, in particular immunosuppressive, anti-inflammatory and anti-parasitic activity. The first of the cyclosporins to be isolated and the "parent" compound of the class, was the naturally occurring fungal metabolite Cyclosporine, also known as cyclosporin A, of formula A

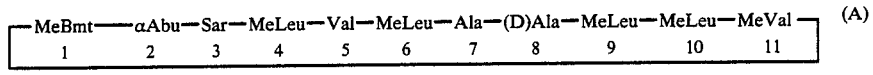

wherein —MeBmt— represents the N-methyl-(4R)-4-but-2E-en-1-yl-4-methyl-(L)threonyl residue of formula B

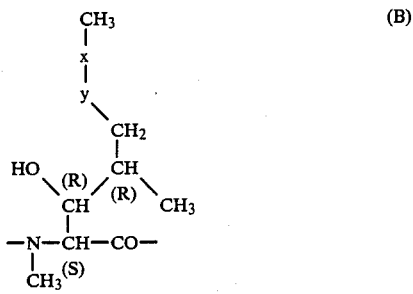

in which —x—y— is —CH=CH— (trans).

Since the original discovery of Cyclosporine a wide variety of naturally occurring cyclosporins have been isolated and identified and many further non-natural cyclosporins have been prepared by total- or semi-synthetic means or by the application of modified culture techniques. The class comprised by the cyclosporins is thus now substantial and includes for example the naturally occurring cyclosporins A through Z [c.f. Kobel et al. European Journal of applied Microbiology and Biotechnology 14, 237–240 (1982) and poster presented by Traber et al., 24th. Interscience Conference on Antimicrobial Agents and Chemotherpy, Washington, Oct. 8–10, (1984)]; as well as various non-natural or artificial cyclosporins, including dihydro-cyclosporins (in which the group —x—y— of the —MeBmt— residue—see formula B above—is saturated, e.g. as disclosed in U.S. Pat. Nos. 4,108,985; 4,210,581 and 4,220,641), cyclosporins in which the —MeBmt— residue is present in isomeric or N-desmethyl form [c.f. European Pat. No. 0 034 567 and "Cyclosporin A", Proc. Internat. Conference on Cyclosporin A, Cambridge (U.K.) September 1981, Ed. D. J. G. White, Elsevier Press (1982)—both describing the total-synthetic method for the production of cyclosporins developed by R. Wenger] and cyclosporins in which incorporation of variant amino acids at specific positions within the peptide sequence is effected (c.f. European Pat. No. 0 056 782). Examples of such cyclosporins as disclosed in the above art references include e.g. [Thr]$^2$—, [Val]$^2$—, [Nva]$^2$— and [Nva]$^2$—[Nva]$^5$—Cyclosporine (also known as cyclosporins C, D, G and M respectively), [Dihydro-MeBmt-]$^1$—[Val]$^2$—Cyclosporine (also known as dihydrocyclosporin D) and [(D)Ser]$^8$— and [Dihydro-MeBmt-]$^1$—[(D)-Ser]$^8$—Cyclosporine.

[In accordance with now conventional nomenclature for the cyclosporins, these are defined throughout the present specification and claims by reference to the structure of Cyclosporine (i.e. cyclosporin A). This is done by first indicating those residues in the molecule which differ from those present in Cyclosporine and then applying the term "Cyclosporine" to characterise the remaining residues which are identical to those present in Cyclosporine. At the same time the term —dihydro—MeBmt— is employed to designate the residue of formula B above in which —x—y— is —CH$_2$—CH$_2$—. Thus [Dihydro—MeBmt]$^1$—[Val]$^2$—Cyclosporine is the cyclosporin having the sequence shown in formula A, but in which —MeBmt— [formula B, —x—y—=—CH=CH— (trans)] at the 1-position is replaced by —dihydro—MeBmt— [formula B, —x—y—=—CH$_2$—CH$_2$—] and —αAbu— at the 2-position is replaced by —Val—. Similarly [(D)Ser]$^8$—Cyclosporine is the cyclosporin having the sequence shown in formula A, but in which —(D)Ala— at the 8-position is replaced by —(D)Ser—.

In addition, amino acid residues referred to by abbreviation, e.g. —Ala—, —MeVal— etc . . . are, in accordance with conventional practice, to be understood as having the (L)-configuration unless otherwise indicated. Residue abbreviations preceded by "Me", as in the case of —MeLeu— represent N-methylated residues. The individual residues of the cyclosporin molecule are numbered, as in the art, clockwise and starting with the residue —MeBmt— or —dihydro—MeBmt— in position 1. The same numerical sequence is employed throughout the present specification and claims.]

In accordance with the present invention it has now been found that novel cyclosporins may be obtained having pharmaceutical utility, in which the residue at the 8-position comprises an acyloxy α-amino acid residue having the (D)-configuration.

Accordingly, in its broadest aspect, the present invention provides: a cyclosporin wherein the amino acid residue at the 8-position is a (D)-acyloxy-α-amino acid residue, i.e. the residue of an α-amino acid of the (D)-series wherein the side chain attaching to the α-carbon atom is acyloxy-substituted.

Preferably the amino acid residue at the 8-position is a (D)-β-acyloxy-α-amino acid residue, i.e. the residue of an α-amino acid of the (D)-series having an acyloxy group attached at the β-carbon atom.

Preferred (D)-β-acyloxy-α-amino acid residues are those of formula II

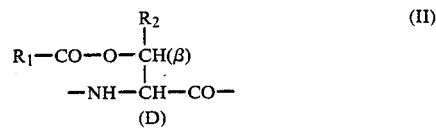

wherein $R_1$ is hydrogen, $C_{1-4}$alkyl or phenyl and
$R_2$ is hydrogen or methyl.

Especially preferred cyclosporins in accordance with the present invention are those wherein the amino acid residue at the 8-position is an O-acyl-(D)-seryl or O-acyl-(D)-threonyl residue, in particular an O-acyl-(D)seryl or O-acyl-(D)-threonyl residue of formula II above.

In one group of cyclosporins in accordance with the present invention, the amino acid residue at the 8-position is an O-acyl-(D)-seryl residue, especially an O-acyl-(D)-seryl residue wherein the acyl moiety has the formula $R_1$—CO— in which $R_1$ has the meaning given above.

In a second group of cyclosporins in accordance with the present invention, the amino acid residue at the 8-position is a (D)-β-acyloxy-α-amino acid residue, especially an O-acyl-(D)-seryl residue, more especially an O-acyl-(D)-seryl residue wherein the acyl moiety has the formula $R_1$—CO— in which $R_1$ is hydrogen or $C_{1-4}$alkyl, and the residue at the 5-position is an (L)-norvalyl residue.

Most preferred are cyclosporins of formula I

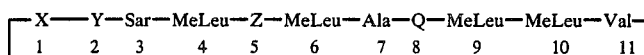

wherein
X is —MeBmt— or —dihydro—MeBmt—,
Y is —αAbu—, —Ala—, —Thr—, —Val— or —Nva—
Z is —Val— or —Nva—, and
Q is a residue of formula II as defined above.

In formula I, Q is preferably an O-acyl-(D)-seryl or O-acyl-(D)-threonyl residue wherein the acyl moiety has the formula $R_1$—CO— in which $R_1$ has the meaning given for formula II. Y is preferably —αAbu—, —Thr—, —Val— or —Nva—.

A group of cyclosporins in accordance with the present invention are those of formula I as defined above, wherein Y is —αAbu— or —Nva—, Z is —Val— and $R_2$ is hydrogen.

A further group of cyclosporins in accordance with the present invention are those of formula I as defined above, wherein Y is —αAbu— or —Nva—, Z is —Nva—, $R_1$ is hydrogen or $C_{1-4}$alkyl and $R_2$ is hydrogen.

The present invention also provides a process for the production of a cyclosporin wherein the amino acid residue at the 8-position is a (D)-acyloxy-α-amino acid residue, for example a (D)-β-acyloxy-α-amino acid residue, e.g. for the production of a cyclosporin of formula I as defined above, which process comprises:

(a) Acylating a cyclosporin wherein the amino acid residue at the 8-position is a (D)-hydroxy-α-amino acid residue, for example a (D)-β-hydroxy-α-amino acid residue, e.g. acylating a cyclosporin of formula III

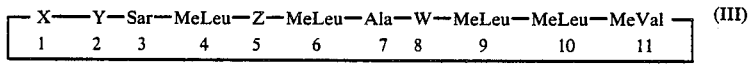

wherein X, Y and Z have the meanings given above for formula I and W is a residue of formula IV

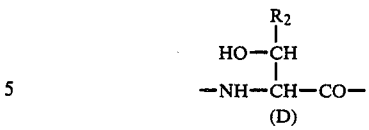

wherein $R_2$ has the meaning given above for formula II, to introduce a group $R_1$—CO—, wherein $R_1$ has the meaning given above for formula II, at the B-position of said residue IV; or (b) Reducing a cyclosporin wherein the amino acid residue at the 1-position is —MeBmt— and the residue at the 8-position is a (D)-acyloxy-α-amino acid residue, for example a (D)-β-acyloxy-α-amino acid residue, to produce the corresponding cyclosporin wherein the residue at the 1-position is —dihydro—MeBmt—, e.g. reducing a cyclosporin of formula I as hereinbefore defined, wherein X is —MeBmt—, to produce the corresponding cyclosporin wherein X is —dihydro—MeBmt—.

Process step (a) above may be carried out in accordance with standard procedures for the acylation of hydroxy groups, for example by reaction with (preferably 2 equivalents or, when Y=—Thr—, 1 equivalent) of an appropriate acyl—, e.g. $C_{1-5}$alkanoyl— or benzoyl-halide, or corresponding -anhydride or, for formylation, by reaction with e.g. acetic-formic anhydride, at a temperature of e.g. from about −10° to 50° C. The reaction is carried out under anhydrous conditions, suitably in the presence of an inert solvent or diluent such as methylene chloride, and in the presence of a condensation agent such as 4-dimethyl-amino-pyridine. In this connection it is to be noted that the reaction proceeds with acylation occurring at the OH group of the amino acid residue at the 8-position, in preference to the hydroxy group of the amino acid residue at the 1-position.

Process step (b) may be carried out analogously to known methods for reducing naturally-occurring cyclosporins to the corresponding dihydrocyclosporins, for example by catalytic hydrogenation, e.g. in accordance with the general methods disclosed in U.K. Patent Specification No. 1,567,201.

Hydrogenation is suitably effected under neutral pH conditions at temperatures of from about 20° to about 30° C. and at atmospheric or slightly elevated pressure, in the presence of a catalyst such as platinum or, preferably, palladium (e.g. palladium on charcoal) in the presence of an inert solvent or diluent such as ethyl acetate or lower aliphatic alkanols such as methanol or isopropanol.

Cyclosporins having a β-hydroxy-α-amino acid residue at the 8-position, in particular [(D)Ser]$^8$-Cyclosporine and [Dihydro-MeBmt]$^1$-[(D)Ser]$^8$-Cyclosporine, suitable for use as starting materials in process step (a) above are known and have been described together with processes for their production, e.g. in the aforementioned European Pat. No. 0 056 782. Other cyclosporins having a hydroxy-α-amino acid residue at the 8-position and required as starting materials for process step (a), may be prepared analogously or in accordance with the general procedures of the cyclosporin total-synthetic method described in European Pat. No. 0 034 567 to which publication 0 056 782 cross-refers, or in accordance with the procedures hereinunder described in particular in the accompanying examples.

The cyclosporins starting materials for use in process step (b) above are obtainable in accordance with the method of process step (a).

Although the cyclosporin starting materials of formula III above specifically disclosed in the accompanying examples are embraced by the broad disclosure of the aforementioned European Pat. No. 0 056 782, certain of these cyclosporins are formally novel over the teachings of that publication, i.e. have never previously been described as such. In accordance with the present invention it has also been found that these cyclosporins possess especially interesting or advantageous biological activity or profile, in particular in relation to immunosuppressive activity, and especially in relation to prevention of transplant, e.g. organ transplant, rejection, e.g. as compared with known cyclosporins of formula III, i.e. cyclosporins of formula III specifically disclosed in European Pat. No. 0 056 782.

Accordingly in a further aspect the present invention also provides a cyclosporin of formula IIIa

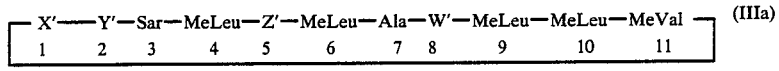

wherein
Y' is —αAbu—, —Thr—, —Val— or —Nva—,
Z' is —Val— or, when Y' is —αAbu— or —Nva—, —Nva—
W' is —(D)Ser— or, when Y' is —αAbu— and Z' is —Val—, —(D)Thr—, and
X' is —MeBmt— or, when Y' is —Thr—, —Val— or —Nva—, Z' is —Val— and W' is 13 (D)Ser—, —dihydro—MeBmt—.

Specific cyclosporins of formula IIIa are:
(a) [(D)Thr]8-Cyclosporine
(b) [Thr]2-[(D)Ser]8-Cyclosporine
(c) [Dihydro-MeBmt]1-[Thr]2-[(D)Ser]8-Cyclosporine
(d) [Val]2-[(D)Ser]8-Cyclosporine
(e) [Dihydro-MeBmt]1-[Val]2-[(D)Ser]8-Cyclosporine
(f) [Nva]2-[(D)Ser]8-Cyclosporine
(g) [Dihydro-MeBmt]1-[Nva]2-[(D)Ser]8-Cyclosporine
(h) [Nva]5-[(D)Ser]8-Cyclosporine; and
(i) [Nva]2-[Nva]5-[(D)Ser]8-Cyclosporine Of the above listed cyclosporins, (a), (b), (e), (f) and (i), and in particular (a), (f) and (i) are of especial interest, having regard to their activity (e.g. immunosuppressive activity)/activity profile, e.g. in relation to cyclosporins specifically disclosed in European Pat. No. 0 056 782.

In addition to the foregoing the present invention also provides a process for the production of a cyclosporin of formula IIIa as defined above, which process comprises: (c) Deprotecting a cyclosporin of formula III as defined above which is in O-protected form;

(d) Cyclising a straight chain undecapeptide comprising the sequence

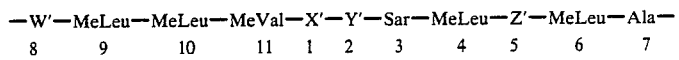

wherein Y', Z', W' and X' have the meanings given above for formula IIIa, said undecapeptide being in unprotected or O-protected form and, when required, carrying out process step c;

(e) For the production of a cyclosporin of formula IIIa wherein
Y' is —Thr—, —Val— or —Nva—,
Z' is —Val— or, when Y' is —Nva—, —Nva—,
W' is —(D)Ser—
and X' is —MeBmt—,
cultivating a [Thr]2-Cyclosporine, [Val]2-Cyclosporine, [Nva]2-Cyclosporine or [Nva]2-[Nva]5-Cyclosporine producing fungus strain in contact with a nutrient medium containing (D)-Serine and isolating the cyclosporin of formula IIIa from the obtained culture medium;

(f) For the production of a cyclosporin of formula IIIa wherein X' is -dihydro-MeBmt, reducing the corresponding cyclosporin of formula IIIa wherein X' is —MeBmt—.

Undecapeptides suitable for use in process step (d) above may be obtained analogously to the general methods described in the above mentioned European Pat. No. 0 056 782, e.g. in relation to the flow chart to Example 1a thereof, by combination of the peptide sequence comprising residues 8 through 11 of the cyclosporin molecule with the sequence comprising residues 1 through 7 but with the required substitution of residues at positions 2 and/or 5 and/or 8. Suitably the —(D)Ser— or —(D)Thr— residue at the 8-position is in O-protected form, e.g.in the form of the O-t-butyl derivative. Cyclisation is carried out using the particular techniques described in the said European Patent, with final removal of O-protecting groups when present [process step (c)] in accordance with techniques known in the art of peptide chemistry.

The preferred fungus strain for use in the method of process step (e) is the strain NRRL 8044 of the species *Tolypocladium inflatum* (Gams), a culture of which has been deposited with the United States Department of Agriculture (Northern Research and Development Division), Peoria, Ill., USA and is freely available to the public. A further culture of this strain has been deposited with the Fermentation Research Institute, Inage, Chiba City, Japan, under the code number FRI FERM-p No. 2796. The morphological characteristics of said strain, originally classified as belonging to the species *Trichoderma polysporum* (Link ex Pers.), as well as methods for the preparation and maintainance of pre- and sub-cultures are fully described e.g. in UK patent specification No. 1,491,509.

In accordance with process step (e) the selected strain [e.g. *Tolypocladium inflatum* (Gams)] is suitably maintained for a period of ca. 2 weeks at a temperature of ca. 27° C. in a culture medium such as described in the following examples, in the presence of added (D)- or (D,L)-serine. The amino acid precursor is suitably added in an amount of from about 1 to about 15 g, more preferably from about 4 to about 10 g/liter culture medium. Suitably the culture medium also contains added amino acid precursor for the residue present in the desired cyclosporin at position 2, e.g. in amounts of from about 6.0 to about 10.0, preferably about 8.0 g/liter culture medium. Following incubation the culture is harvested and the obtained cyclosporin of formula IIIa extracted in accordance with known techniques, e.g. by comminution of conidia and mycelia, followed by extractive and/or absorptive isolation. The initially obtained, raw cyclosporin may thereafter be purified e.g. chromatographically and/or by recrystallisation, in particular to effect separation from other cyclosporin contaminants in particular "natural cyclosporin" contaminants.

Process step (f) above may be carried out e.g. using the same methods hereinbefore described in relation to process step (b).

The following examples are illustrative of the processes of the present invention.

EXAMPLE 1

Synthesis of [(O-acetyl)-(D)Ser]$^8$-Cyclosporine [Formula I: X=—MeBmt—, Y=—αAbu—, Z=—Val—, Q=—O—acetyl—(D)Ser—]

20 mg 4-dimethylaminopyridine are added to 47 mg [(D)Ser$^8$]-Cyclosporine (prepared in accordance with the method described in Example 1 or 3 of the above mentioned European Pat. No. 0 056 782) dissolved in 3 ml methylene chloride. 6.1 mg of freshly distilled acetylchloride in 1 ml methylene chloride are then added and the obtained reaction mixture is stirred for 1 hour at room temperature. The reaction mixture is diluted with 50 ml methylene chloride and shaken with 30 ml H$_2$O. The organic phase is separated, dried over Na$_2$SO$_4$, filtered off and evaporated. The residue is filtered on 60 g silica gel (0.062-0.20 mm) using methylene chloride/5% methanol as eluant and collected in 25 ml fractions. The title compound is recovered from fractions 4 to 8 by thin layer chromatography using CHCl$_3$/5 % methanol as carrier phase: $[\alpha]_D^{20} = -202°$ (c=0.92 in CHCl$_3$).

EXAMPLE 2

The following compounds may be prepared analogously to example 1 starting from the corresponding non-acylated cyclosporin:

2.1 [(O-benzoyl-(D)Ser]$^8$-Cyclosporine [Formula I: X=—MeBmt—, Y=—αAbu—, Z=—Val—, Q=—O—benzoyl—(D)Ser—]: $[\alpha]_D^{20} = -220°$ (c=1.0 in CHCl$_3$);

2.2 [O-acetyl-(D)Thr]$^8$-Cyclosporine Formula I: X=—MeBmt—, Y=—αAbu—, Z=—Val—, Q=—O-acetyl-(D)-Ser-]: $[\alpha]_D^{20} = -219°$ (c=1.0 in CHCl$_3$);

2.3 [Nva]$^2$-[O-acetyl-(D)Ser]8-Cyclosporine [Formula I: X=—MeBmt—, Y=—Nva—, Z=—Val—, Q=-O-acetyl-(D)Ser-]: $[\alpha]_D^{20} = -240°$ (c=1.0 in CHCl$_3$)/−233° (c=0.8 in CHCl$_3$)/−177° (c=0.76 in CH$_3$OH): m.p.=143°-147° C.

2.4 [Val]$^2$-[O-acetyl-(D)Ser]$^8$-Cyclosporine [Formula I: X=—MeBmt—, Y=—Val—, Z=—Val—, Q=-O-acetyl-(D)Ser-]: $[\alpha]_D^{20} = -219°$ (c=0.9 in CHCl$_3$);

2.5 [Nva]$^5$-[O-acetyl-(D)Ser]$^8$-Cyclosporine [Formula I: X=—MeBmt—, Y=—αAbu—, Z=—Nva—, Q=-O-acetyl-(D)Ser-]: $[\alpha]_D^{20} = -215°$ (c=1.0 in CHCl$_3$);

2.6 [Nva]$^2$-[Nva]$^5$-[O-acetyl-(D)Ser]$^8$-Cyclosporine [Formula I: X=—MeBmt—, Y=—Nva—, Z=—Nva—, Q=-O-acety-(D)Ser-]: $[\alpha]_D^{20} = -196.9°$ (c=1.0 in CHCl$_3$); and 2.7 [Thr]$^2$-[O-acetyl-(D)Ser]$^8$-Cyclosporine [Formula I: X=—MeBmt—, Y=—Thr—, Z=—Val— Q=-O-acetyl-(D)Ser-]: $[\alpha]_D^{20} = -251°$ (c=0.86 in CHCl$_3$)/−174° (c=0.81 in CH$_3$OH): m.p.=143°-146° C.

EXAMPLE 3

Synthesis of [Dihydro-MeBmt]$^1$—[O-acetyl-(D)Ser]$^8$-Cyclosporine [Formula I: X=—dihydro—MeBmt—, Y=—αAbu—, Z=—Val—, Q=-O-acetyl-(D)Ser-]

54 mg of [(O-acetyl)-(D)Ser$^8$]-Cyclosporine in 10 ml ethanol are hydrogenated using 10 mg palladium/charcoal (10%) at room temperature and under normal pressure. After 20 hours the obtained reaction solution is filtered through a thin layer of talc and the ethanol is evaporated off under vacuum. After further drying under high vacuum, the title compound is obtained: $[\alpha]_D^{20} = -205.8°$ (c=1.02 in CHCl$_3$).

EXAMPLE 4

The following compounds may be prepared either analogously to example 1, starting from the corresponding non-acylated cyclosporin or analogously to example 3, by hydrogenation of the corresponding cyclosporin described in example 2:

4.1 [Dihydro-MeBmt]$^1$-[Nva]$^2$-[O-acetyl-(D)Ser]$^8$-Cyclosporine [Formula I: X=—dihydro—MeBmt13 , Y=—Nva—, Z=—Val—, Q=-O-acetyl-(D)Ser-]: m.p.=139°-141° C.; $[\alpha]_D^{20} = -225°$ (c=0.88 in CHCl$_3$)/−163° (c=0.76 in CH$_3$OH);

4.2 [Dihydro-MeBmt]$^1$-[Val]$^2$-[O-acetyl-(D)Ser]$^8$-Cyclosporine [Formula I: X=—dihydro—MeBmt—, Y=—Val—, Z=—Val—, Q=-O-acetyl-(D)Ser-]: $[\alpha]_D^{20} = -210°$ (c=0.85 in CHCl$_3$); and 4.3 [Dihydro-MeBmt]$^1$-[Thr]$^2$-[O-acetyl-(D)Ser]$^8$-Cyclosproine [Formula I: X=—dihydro—MeBmt—, Y=—Thr—, Z=—Val—, Q=O-acetyl-(D)Ser-]: $[\alpha]_D^{20} = -241°$ (c=1.0 in CHCl$_3$)/−162° (c=1.0 in CH$_3$OH): m.p.=148°-150° C.

Preparation of starting materials

EXAMPLE 5

The following compounds required as starting materials for the production of the compounds of examples 2.2 through 2.7 may be prepared analogously to the known compound [(D)Ser]$^8$-Cyclosporine, the preparation of which is described in Example 1 of European Pat. No. 0 056 782, with substitution of the appropriate residues at positions 2 and/or 5 and/or 8 in the process sequence set forth in the flow chart to Example 1a of said patent:

5.1 [(D)Thr]$^8$-Cyclosporine [Formula IIIa: X'=—MeBmt—, Y'=—αAbu—, Z'=—Val—, W'=—(D)Thr—]: $[\alpha]_D^{20} = -248.7°$ (c=1.0 in CHCl$_3$);

5.2 [Nva]$^2$-[(D)Ser]$^8$-Cyclosporine [Formula IIIa: X'=—MeBmt—, Y'=—Nva—, Z'=—Val—, W'=—(D)Ser—]: m.p.=150°-153° C.; $[\alpha]_D^{20} = -262°$ (c=0.71 in CHCl$_3$)/−191° (c=0.73 in CH$_3$OH);

5.3 [Val]$^2$-[(D)Ser]$^8$-Cyclosporine [Formula IIIa: X'=—MeBmt—, Y'=—Val—, Z'=—Val—, W'=—(D)Ser—]: $[\alpha]_D^{20}=-257°$ (c=1.0 in CHCl$_3$)/−255° (c=0.45 in CHCl$_3$)/−189° (c=0.42 in CH$_3$OH): m.p.=136°-140° C.

5.4 [Nva]$^5$-[(D)Ser]$^8$-Cyclosporine [Formula IIIa: X'=—MeBmt—, Y'=—αAbu—, Z'=—Nva—, W'=—(D)Ser—]: $[\alpha]_D^{20}=-212°$ (c=1.0 in CHCl$_3$);

5.5 [Nva]$^2$-[Nva]$^5$-[(D)Ser]$^8$-Cyclosporine [Formula IIIa: X'=—MeBmt—, Y'=—Nva—, Z'=—Nva—, W'=—(D)Ser—] $[\alpha]_D^{20}=-217°$ (c=1.0 in CHCl$_3$); and 5.6 [Thr]$^2$-[(D)Ser]$^8$-Cyclosporine [Formula IIIa: X'=—MeBmt—, Y'=—Thr—, Z'=—Val—, W'=—(D)Ser—]: $[\alpha]_D^{20}=-258°$ (c=0.39 in CHCl$_3$)/−178° (c=0.40 in CH$_3$OH): m.p.=147°-152° C.

EXAMPLE 6

The compound of example 5.2 may alternatively be produced microbiologically as follows:

(a) 10 liters of a nutrient medium containing 50 g maltose; 5 g (DL)-norvaline; 8 g (D)-serine; 0.75 g KH$_2$PO$_4$; 0.5 g MgSO$_4$.7H$_2$O; 0.1 CaCl$_2$.6H$_2$O and 8 g caseinpeptone per liter are inoculated with 1 liter of a suspension of conidia and mycelia of the fungus strain NRRL 8044 taken from a 3 day old pre-culture. The incoculated production-medium is filled in 100 ml portions into 100 Erlenmeyer flasks which are then incubated for 14 days at 27° on an agitator rotating at 180 r.p.m. The mycelium is separated from the culture medium and extracted in a Turrax apparatus by crushing and stirring with 3×3 liters of 90% methanol. The crushed mycelium is separated from the solvent by suction-filtration and the combined filtrates are concentrated by evaporation under vacuum at a temperature of 40° C. until the vapour consists mainly of water alone. The obtained mixture is extracted 4× using 0.5 liter 1,2-dichloroethane at each extraction and the combined 1,2-dichloroethane solutions are concentrated by evaporation under vacuum at a temperature of 40° C.

The obtained residue is subjected to gel filtration on Sephadex LH-20 (1.4 kg; Pharmacia) with methanol, and collected in 280 ml fractions. Fractions 9-11, containing a cyclosporin mixture are pooled and then separated by silica gel column chromatography (1 kg of silica gel, granulate size 0.063-0.2 mm, "Merck") using water saturated ethyl acetate as eluent (fractions of 500 ml). In accordance with their polarity, [Nva$^2$]-Cyclosporine elutes first (fractions 7-9), followed by a mixture comprising [Nva$^2$]-[(D)Ser$^8$]-Cyclosporine and Cyclosporine. Separation of [Nva$^2$]-[(D)Ser$^8$]-Cyclosporine and Cyclosporine is achieved by silica gel chromatography (280 g, "Merck", 0.63-0.2 mm) using chloroform/methanol (98:2) as eluent (fractions of 100 ml). Fractions 20-30, containing crude [Nva$^2$]-[(D)Ser$^8$]-Cyclosporine, are further purified by medium-pressure chromatography on a reversed-phased silica gel column ("Merck" LiChropep RP 18, 260 g, granulate size 0.04-0.063 mm) with methanol/water (85:15) as eluent, with collection in 25 ml fractions. The combined fractions 45-55 yield pure [Nva$^2$]-[(D)Ser$^8$]-Cyclosporine as an amorphous white powder.

The pre-culture required for the above process may be obtained as follows:

(b) The spore and mycelium suspension used for inoculation is produced from a culture of the originally isolated strain NRRL 8044, cultivated for 21 days at 27° C. on an agar medium containing 20 g of malt extract, 20 g of agar, 4 g of yeast extract per liter of demineralised water. The spores of this culture are taken up in a physiological NaCl solution to give a final concentration of 5×10$^6$ spores/ml. 10 ml of this suspension are used for inoculation of 1 liter of a nutrient solution having the same composition as the culture medium of Example 6a, with the exception of the (D)-serine and (DL)-norvaline components, and incubation is effected at 27° C. for 3 days on a rotary shaker (200 r.p.m.). This culture is used as inoculum for the producing culture, [Nva$^2$]-[(D)Ser$^8$]-Cyclosporine may be produced on fermenter scale as follows:

(c) Ca. 10$^9$ spores from an agar slant of the strain NRRL 8044 are transferred into a stainless-steel-fermenter containing 20 liters of a pre-culture-medium comprising:

| Fructose | 75 g |
| Amber EHC | 25 g |
| KH$_2$OP$_4$ | 5 g |
| KCl | 2.5 g |
| Dist. Water to (pH = 5,5) | 1 liter | previously sterilized for 20 minutes at 120° C. Favourable incubation conditions are a temperature of 27° C., airflow of 16 liters per minute at an overpressure of 0.5 bar and stir rotation of 200 r.p.m. The developing pre-culture is incubated for 6 days and 15 liters are then transferred to a stainless-steel-fermenter holding 300 liters of production medium comprising:

| Maltose | 75 g |
| Amber EHC | 25 g |
| KH$_2$PO$_4$ | 5 g |
| KCl | 2,5 g |
| (DL)-norvaline | 5 g |
| (D)-serine | 8 g |
| Dist. Water to (pH = 5,5) | 1 liter | previously sterilized for 20 minutes at 120° C.

The culture is held at a temperature of 27° C., aerated with 120 liters air per minute at an overpressure of 0.5 bar and stirred at 70 r.p.m. Foam control is performed by addition of a silicone emulsion.

After incubation for 14 days the culture, which has a total volume of 275 liters is cooled to 10° C. and the mycelia removed using a Westfalia separator. The filtrate is extracted by stirring 2× with ethyl acetate, the extracts are washed with a little water, combined and dried under vacuum. The mycelium is combined with methanol, homogenised and filtered. This extraction is repeated 2× using 90% methanol. The methanolic extracts are combined and, with addition of water, concentrated under vacuum. The remaining, aqueous concentrate is extracted 2× with ethyl acetate, the extracts washed with a little water, combined and concentrated under vacuum. The extracted aqueous phase is re-extracted 2× with ethyl acetate/isopropanol (8:2). These extracts are combined and again evaporated under vacuum.

The mycelial and filtrate extracts are filtered using 50× the amount of Sephadex LH-20 with methanol as eluant. The peak-fractions are then purified chromatographically using 100× the amount of silica gel 60 (particle size=0.04-0.063 mm) using water-saturated ethyl acetate as eluant. [Nva$^2$]-Cyclosporine elutes first followed by Cyclosporine and [Nva$^2$]-(D)-Ser$^8$]-Cyclosporine. These later fractions are subjected to further chromatographic purification using 140× the amount of silica gel 60 (particle size 0.063–0.20 mm) and chloroform/methanol (98:2) as eluant, to yield pure [Nva$^2$]-[(D)Ser$^8$]-Cyclosporine.

EXAMPLE 7

The compound of example 5.3 may also be produced microbiologically proceeding analogously to example 6(a) but with the following modifications:

(a) In the nutrient medium—replacement of (DL)-norvaline with 10 g (L)-valine. Following separation of the mycelium from the culture medium—extraction as follows:

The crushed mycelium is separated from the solvent by suction-filtration and the combined filtrates are concentrated (under addition of water) by evaporation under vacuum at a temperature of 40° C. until the vapour consists mainly of water alone. The obtained mixture is extracted 3× using 5 liters ethyl acetate at each extraction and the combined ethyl acetate solutions are concentrated by evaporation under vacuum at a temperature of 40° C.

The obtained residue is subjected to gel filtration on Sephadex LH-20 (1.4 kg; Pharmacia) with methanol. Those fractions which contain a cyclosporin mixture are pooled and then separated by silica gel column chromatography (3 kg of silicagel, granulate size 0.020–0.045 mm, "Grace") using water-saturated ethyl acetate as eluent. In accordance with their polarity, [Val$^2$]-Cyclosporine elutes first followed by a mixture comprising [Val$^2$]-[(D)Ser$^8$]-Cyclosporine as the major component. Further purification of [Val$^2$]-[(D)Ser$^8$]-Cyclosporine is achieved by silica gel chromatography (80 g, "Grace", 0.020–0.0045 mm) using acetone/hexane (1:1) as eluent. Those fractions containing crude [Val$^2$]-[(D)Ser$^8$]-Cyclosporine, are further purified by medium-pressure chromatography on a reversed-phased silica gel column ("Merck" LiChroprep RP 18, 160 g, granulate size 0.04–0.063 mm) with methanol/water (80:20) as eluent, yielding pure [Val$^2$]-[(D)Ser$^8$]-Cyclosporine as an amorphous white powder.

(b) The pre-culture required is obtained as in example 6(b). [Val$^2$]-[(D)Ser$^8$]-Cyclosporine may be produced on fermenter scale proceeding analogously to example 6(c) but with the following modifications:

(c) In the production medium—replacement of (DL)-norvaline with 10 g (L)-valine. Following combination of the mycelium with methanol, homogenisation and filtration (repeated 2× using 90% methanol)—further processing as follows:

The methanolic extracts are combined and, with addition of water, concentrated under vacuum. The remaining, aqueous concentrate is extracted 3× with ethyl acetate, the extracts washed with a little water, combined and evaporated under vacuum.

The mycelial and filtrate extracts are filtered using 50× the amount of Sephadex LH-20 with methanol as eluant. The peak-fractions are then purified chromatographically using 40× the amount of silica gel 60 (particle size=0.04–0.063 mm) using water-saturated ethyl acetate as eluant. [Val$^2$]-Cyclosporine elutes first followed by Cyclosporine and [Val$^2$]-[(D)Ser$^8$]-Cyclosporine. These later fractions are subjected to further chromatographic purification using 100× the amount of silica gel 60 and acetone/hexane (1:1) as eluant, and medium-pressure chromatography on reversed-phased silica gel ("Merck" LiChroprep RP 18, granulate size 0.04–0.063 mm) with methanol/water (80:20) as eluant, to yield pure [Val$^2$]-[(D)Ser$^8$]-Cyclosporine.

EXAMPLE 8

The compound of example 5.6 may also be produced microbiologically proceeding analogously to example 6(a) but with the following modifications:

(a) In the nutrient medium—replacement of (DL)-norvaline with 5 g (L)-threonine. Following incubation—extraction as follows:

The mycelium is separated from the culture medium and extracted in a Turrax apparatus by crusing and stirring with 3×9 liters of 90% methanol. The crushed mycelium is separated from the solvent by suction-filtration and the combined filtrates are concentrated (under addition of water) by evaporation under vacuum at a temperature of 40° C. until the vapour consists mainly of water alone. The obtained mixture is extracted 3× using 5 liters ethyl acetate at each extraction and the combined ethyl acetate solutions are concentrated by evaporation under vacuum at a temperature of 40° C.

The obtained residue is subjected to gel filtration on Sephadex LH-20 (2 kg; Pharmacia) with methanol. Those fractions containing a cyclosporin mixture are pooled and then separated by silica gel column chromatography (2 kg of silica gel, granulate size 0.02–0.045 mm, "Grace") using water-saturated ethyl acetate as eluent. In accordance with their polarity, Cyclosporine elutes first, followed by [(D)Ser$^8$]-Cyclosporine, followed by [Thr$^2$]-Cyclosporine and finally [Thr$^2$]-[(D)Ser$^8$]-Cyclosporine in crude form. Further purification of [Thr$^2$]-[(D)Ser$^8$]-Cyclosporine is achieved by silica gel chromatography (50 g, "Grace", 0.02–0.45 mm) using acetone/hexane (2:1) as eluent yielding pure [Thr$^2$]-[(D)Ser$^8$]-Cyclosporine as an amorphous white powder.

(b) The pre-culture required is obtained as in example 6(b). [Thr$^2$]-[(D)Ser$^8$]-Cyclosporine may be produced on fermenter scale proceeding analogously to example 6(c) but with the following modifications:

(c) In the production medium—replacement of (DL)-norvaline with 5 g (L)-threonine. Following incubation and removal of the mycelia using a Westfalia separator—further processing as follows:

The mycelium is combined with methanol, homogenised and filtered. This extraction is repeated 2× using 90% methanol. The methanolic extracts are combined and, with addition of water, concentrated under vacuum. The remaining, aqueous concentrate is extracted 3× with ethyl acetate, the extracts washed with a little water, combined and concentrated under vacuum.

The mycelial extract is filtered using 50× the amount of Sephadex LH-20 with methanol as eluant. The peak-fractions are then purified chromatographically using 30× the amount of silica gel 60 (particle size=0.04–0.063 mm) using water-saturated ethyl acetate as eluant. Cyclosporine elutes first followed by [(D)Ser$^8$]-Cyclosporine, followed by [Thr$^2$]-Cyclosporine and finally [Thr$^2$]-[(D)Ser$^8$]-Cyclosporine. These later fractions are subjected to further chromatographic purification using 250× the amount of silica gel 60 (particle size 0.02–0.045 mm) and acetone/hexane (2:1) as eluant, to yield pure [Thr$^2$]-[(D)Ser$^8$]-Cyclosporine.

EXAMPLE 9

The following compounds, which may be employed as starting materials for production of the compounds of examples 4.1 through 4.3, may be prepared from the indicated cyclosporins of examples 5 through 7, proceeding analogously to example 3.

9.1 [Dihydro-MeBmt]$^1$-[Nva]$^2$-[(D)Ser]$^8$-Cyclosporine [Formula IIIa: X'=—dihydro—MeBmt—, Y'=—Nva—, Z'=—Val—, W'=—(D)Ser—]—prepared from the product of example 5.2 or 6: $[\alpha]_D^{20} = -251°$ (c=1.23 in CHCl$_3$)/−179° (c=1.16 in CH$_3$OH): m.p.=155°-157° C.

9.2 [Dihydro-MeBmt]$^1$-[Val]$^2$-[(D)Ser]$^8$-Cyclosporine [Formula IIIa: X'=—dihydro—MeBmt—, Y'=—Val—, Z'=—Val—, W'=—(D)Ser—]—prepared from the product of example 5.3 or 7: $[\alpha]_D^{20} = -224°$ (c=1.0 in CHCl$_3$).

9.3 [Dihydro-MeBmt]$^1$-[Thr]$^2$-[(D)Ser]$^8$-Cyclosporine [Formula IIIa: X'=—dihydro—MeBmt—, Y'=—Thr—, Z'=—Val—, W'=—(D)Ser—]—prepared from the product of example 5.6 or 8: $[\alpha]_D^{20} = -262°$ (c=0.73 in CHCl$_3$)/−173° (c=0.79 in CH$_3$OH): m.p.=156°-158° C.

End product cyclosporins, e.g. of formula I, as hereinbefore defined and described exhibit pharmacological activity as may be shown in the following test methods:

1. Immunosuppressive activity 1.1 Local haemolysis in vitro in gel [R. I. Mishell and R. W. Dutton, J. Exp. Medicine, 126, 423–442 (1976)]. Cyclosporins of formula I in accordance with the invention inhibit haemolysis zones compared with untreated controls at concentrations of from 0.01 to 10.0 μg/ml.

1.2 Lymphocyte stimulation test according to Janossy and Greaves [Clin. Exp. Immunol., 9, 483 (1971) and 10, 525 (1972)]: Cyclosporins of formula I in accordance with the invention inhibit concanavalin A stimulated DNA-synthesis (inhibition of H$^3$-thymidine incorporation), cell-proliferation and blastogenesis in mouse-spleen lymphocytes compared with untreated controls at concentrations of from 0.001 to 10.0 μg/ml.

1.3 Mixed lymphocyte reaction [Bach et al., J. Exp. Med. 136, 1430 (1972)]: The reaction (i.e. proliferation and differentiation) of lymphocytes [mouse (Balb/c) spleen cells] on co-incubation for 5 days, with allogenic spleen cells from irradiated mice (CBA ♀) is measured in the presence and absence of test-substance. Reaction in the absence of test-substance serves as control and is taken as 100%. Reaction in the presence of test-substance is expressed as the % change compared with the 100% control reaction. Inhibition of reaction is observed using cyclosporins of formula I in accordance with the invention at a concentration of from 0.001 to 10.0 μg/ml$^{-1}$.

1.4 Suppression of organ-rejection: Kidneys from donor rats (F 344, ♀) are transplanted in recipient (Wistar-Furth, ♀) rats. Test-substance is administered p.o. to recipient rats for 14 days, after which treatment is discontinued. Test animals are subjected to bilateral nephrectomy seven days after transplant. Since the life of test animals depends on acceptance and functioning of the grafted organ, increase in survival time compared with control animals receiving placebo only serves as a parameter for test-substance efficiency. In the above test method animals receiving cyclosporins of formula I in accordance with the present invention at dosages of from 2.5 to 10 mg/kg p.o. exhibit a survival span from >60 to >250 days as compared with untreated controls all of which die as a result of organ rejection within ca. 9 to 10 days.

2. Anti-inflammatory activity

Anti-inflammatory activity may be shown in the adjuvant arthritis test in the rat. For this test adjuvant arthritis is induced according to the method of Pearson and Wood, "Arthr. Rheum" 2, 440 (1959). Cyclosporins of formula I in accordance with the invention are active in this test against developing and established arthritis at doses of from 10 to 30 mg/kg/day p.o.

3. Anti-parasitic activity

Anti-malaria test according to L. Rane, "Chemotherapy and Drug Resistance in Malaria" ed. W. Peters, Academic Press, New York, 1970. Mice (OF1: male) are infected on day 0 with 0.2 ml of a suspension containing 10$^7$ parasitic cells of the species Plasmodium berghei (strain NK 65) administered i.p. Test substance is administered s.c. on day 3, at varying dosages using 5 to 10 mice/dose. The survival time is recorded, and the minimum effective dosage (MED) calculated by comparison of survival time with that for untreated controls. For controls, survival time=ca. 7 days. The MED is the dosage at which survival time is doubled. Cyclosporins of formula I in accordance with the invention are effective in this test at dosages of form 25 to 100 mg/kg/day, s.c.

In view of their immunosuppressive activity, end product cyclosporins, e.g. of formula I, are useful for the prophylaxis and treatment of diseases and conditions requiring a reduction of the immune response. Thus they may be used to suppress the proliferation of lymphocytes and immunocytes, e.g. in treatment of autoimmune diseases or in preventing the rejection of transplants, e.g. skin, lung, heart, heart-lung, bone-marrow, kidney, spleen and corneal transplants.

Specific auto-immune diseases for which the cyclosporins of formula I are useful include all of those for which treatment with Cyclosporine has been proposed or used, for example, aplastic anaemia, pure red cell anaemia, idiopathic thrombocytopaenia, systemic lupus erythematodes, polychondritis, sclerodoma, Wegener granulamatosis, chronic active hepatitis, myasthenia gravis, psoriasis, Steven-Johnson syndrome, idiopathic sprue, Crohn's disease, Graves opthalmopathy, sarcoidosis, multiple sclerosis, primary billiary cirrhosis, primary juvenile diabetes, uveitis posterior, interstitial lung fibrosis and psoriatic arthritis.

In view of their anti-inflammatory activity, end product cyclosporins, e.g. of formula I, are also useful for the treatment of inflammatory conditions, in particular inflammatory conditions with an aetiology comprising or including an auto-immue component, e.g. for the treatment of arthritis and rheumatic diseases such as polyarthritis chronica progrediens.

In view of their anti-parasitic activity, end product cyclosporins, e.g. of formula I, are also useful as anti-parasitic agents, i.e. for the treatment of parasitic infection of varying type, in particular for the treatment of protozoan as well as trematodal and nematodal parasitic infection. Specific types of parasitic infection which cyclosporins may be employed to treat include all of those for which treatment with Cyclosporine has been previously proposed in the literature, including schistomosomiasis, filariasis, leishmania, coccidioidomycosis and in particular malaria.

For the above-mentioned indications dosages will of course, vary depending on the mode of administration, the particular condition to be treated and the therapy desired. In general however, satisfactory results are obtained when administered at a daily dosage of from about 1 up to about 100, preferably up to about 50, most preferably up to about 10 mg/kg animal body weight, conveniently administered once or in divided doses 2 to 3 times a day, or in retard form. For the larger mammals, the total daily dosage is in the range of from about 75 up to about 5,000, preferably up to about 2,000 and most preferably up to about 1,500 mg and unit dosage forms, e.g. for oral administration, suitably comprise from about 25 up to about 2,500, preferably up to about 1,000 and most preferably up to about 800 mg cyclosporin of formula I admixed with a pharmaceutically acceptable diluent or carrier therefor.

In addition to the parameters already noted above a suitable daily dosage for any specific cyclosporin of formula I in any particular indication will depend in particular on its relative potency of activity in relation to the indication, e.g. condition to be treated. The preferred cyclosporin of formula I is the product of example 1 ([O-acetyl-(D)Ser]$^8$-Cyclosporine). Obtained results for this compound in the above described tests are as follows:

| TEST 1.1 $IC_{50}$ ($\mu$g/ml) | TEST 1.2 | TEST 1.3 | TEST 1.4 DOSAGE (mg/kg p.o.) | | | TEST 2 $ED_{50}$ (mg/kg p.o.) | | TEST 3 MED (mg/kg s.c.) |
|---|---|---|---|---|---|---|---|---|
| | | | 5.0 | 7.5 | 10.0 | PT | TT | |
| | | | SURVIVAL RATE IN DAYS (100% Survival) | | | | | |
| 0.057 | <0.008 | <0.04 | >200 | >200 | >200 | <6 | 12 | 25 |

$IC_{50}$=Concentration giving 50% inhibition compared with untreated controls,
PT=preventive treatment, TT=therapeutic treatment
MED=minimum effective dosage.

End product cyclosporins e.g. of formula I may be administered by any conventional route, in particular in accordance with means currently practiced in relation to administration of Cyclosporine, in particular via intravenous infusion e.g. in the case of organ transplant, pre- and immediately post-transplant, as well as during episodes of gastrointestinal disturbance which might otherwise impair absorption, or orally, e.g. in the form of an oral solution.

In accordance with the foregoing the present invention also provides

1. A pharmaceutical composition comprising a cyclosporin of formula I as hereinbefore defined together with a pharmaceutically acceptable diluent or carrier therefor;
2. A cyclosporin of formula I as hereinbefore defined for use as a pharmaceutical, i.e. for use in treatment by surgery or therapy, in particular for use as an immunosuppressant or anti-inflammatory or anti-parasitic agent; as well as
3. A method of inducing immunosuppression, of treating inflammation or of treating parasitic infection, in a subject in need of such treatment, which method comprises administering to said subject an effective amount of a cyclosporin of formula I as hereinbefore defined.

As hereinbefore described the cyclosporins of formula IIIa are also novel and, in addition to their utility as intermediates, exhibit a pharmacological activity and/or profile, in particular in relation to immunosuppressive activity and especially in relation to utility in the prevention of transplant rejection, which renders them of especial interest, e.g. in relation to other cyclosporins specifically disclosed in European Pat. No. 0 056 782. Pharmacological activity of cyclosporins of formula IIIa may be shown e.g. in the above described test methods 1.1, 1.2, 1.3, 2 or 3. Thus cyclosporins of formula IIIa in accordance with the present invention are active:

In test 1.1 above at concentrations of from 0.01 to 10 $\mu$g/ml;
in test 1.2 above at concentrations of from 0.001 to 10 $\mu$g/ml;
in test 1.3 above at concentrations of from 0.001 to 10 $\mu$g/ml;
in test 2 above at doses of from 10 to 30 mg/kg/day p.o.; and
in test 3 above at dosages of from 50 to 100 mg/kg/day s.c.

In view of their immunosuppressive activity cyclosporins of formula IIIa are useful for the prophylaxis and treatment of diseases and conditions requiring a reduction of the immune response, e.g. for the suppression of proliferation of lymphocytes and immunocytes, e.g. in the treatment of auto-immune diseases, for example in the treatment of specific auto-immune diseases hereinbefore recited in relation to the utility of cyclosporins of formula I or in preventing the rejection of transplants, for example of the various specific types hereinbefore recited in relation to the utility of cyclosporins of formula I.

In view of their anti-inflammatory activity, cyclosporins of formula IIIa are also useful for the treatment of inflammatory conditions, in particular inflammatory conditions with an aetiology, comprising or including an auto-immune component, e.g. for the treatment of arthritis and rheumatic diseases such as polyarthritis chronica progrediens.

In view of their anti-parasitic activity, cyclosporins of formula IIIa are also useful as anti-parasitic agents, i.e. for the treatment of parasitic infection of varying type, in particular as hereinbefore described in relation to the utility of cyclosporins of formula I.

For the above mentioned indications, dosages will of course vary depending on the mode of administration, the particular condition to be treated and the therapy desired. In general however, satisfactory results are obtained when administered at a daily dosage of from about 1 to about 100 mg/kg animal body weight, conveniently administered once or in divided doses 2 to 3 times a day, or in retard form. For the larger mammals, the total daily dosage is in the range of from about 75 to about 5,000 mg and unit dosage forms, e.g. for oral administration, suitably comprise e.g. from about 25 to about 2,500 mg cyclosporin of formula IIIa admixed with a pharmaceutically acceptable diluent or carrier therefor.

In addition to the parameters already noted above, a suitable daily dosage for any specific cyclosporin of formula IIIa in any particular indication will depend in particular on its relative potency of activity in relation to the indication, e.g. condition to be treated. The preferred cyclosporins of formula IIIa are A. [(D)Thr]⁸-Cyclosporine (c.f. example 5.1),
B. [Nva]²-[(D)Ser]⁸-Cyclosporine (c.f. examples 5.2 and 6), and
C. [Nva]²-[Nva]⁵-[(D)Ser]⁸-Cyclosporine (c.f. example 5.5).

Obtained results for these in the above described tests are as follows:

| COMPOUND | TEST 1.1 | TEST 1.2 $IC_{50}$ (μg/ml) | TEST 1.3 | TEST 2 $ED_{50}$(mg/kg p.o.) TT | TEST 3 MED (mg/kg s.c.) |
|---|---|---|---|---|---|
| A | 0.033 | 0.0016 | 0.008 | 13 | 50 |
| B | 0.031 | <0.04 | 0.014 | 20 | 50 |
| C | 0.023 | <0.04 | <0.008 | | 100 |

The cyclosporins of formula IIIa may be administered by any conventional route, in particular in accordance with means currently practiced in relation to administration of Cyclosporine, in particular via intravenous infusion, e.g. in the case of organ transplant, pre- and immediately post-transplant, as well as during episodes of gastrointestinal disturbance which might otherwise impair absorption, or orally, e.g. in the form of an oral solution.

In accordance with the foregoing the present invention also provides:

1. A pharmaceutical composition comprising a cyclosporin of formula IIIa as hereinbefore defined together with a pharmaceutically acceptable diluent or carrier therefor.
2. A cyclosporin of formula IIIa as hereinbefore defined for use as a pharmaceutical, i.e. for use in treatment by surgery or therapy, in particular for use as an immunosuppressant or anti-inflammatory or anti-parasitic agent, as well as
3. A method of inducing immunosuppression, of treating inflammation or of treating parasitic infection, in a subject in need of such treatment, which method compounds administering to said subject an effective amount of a cyclosporin of formula IIIa as hereinbefore defined.

I claim:
1. A cyclosporin of formula I

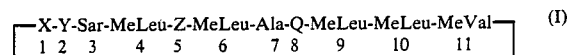

wherein
X is —MeBmt— or —dihydro—MeBmt—,
Y is —αAbu—, —Ala—, —Thr—, —Val— or —Nva—,
Z is —Val— or —Nva—, and
Q is a residue of formula II

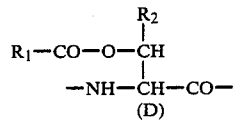

wherein $R_1$ is hydrogen, $C_{1-4}$alkyl or phenyl and $R_2$ is hydrogen or methyl.

2. A cyclosporin according to claim 1 which is [O-acetyl-(D)-Ser]⁸-Cyclosporine.
3. A cyclosporine according to claim 1 which is [Nva]²-[O-acetyl-(D)Ser]⁸-Cyclosporine.
4. A cyclosporin according to claim 1 selected from the group consisting of:
[Dihydro-MeBmt]¹-[O-acetyl-(D)Ser]⁸-Cyclosporine;
[O-benzoyl-(D)Ser]⁸-Cyclosporine; and
[Dihydro-MeBmt]¹-[Nva]²-[O-acetyl-(D)Ser]⁸-Cyclosporine;[Nva]⁵-[O-acetyl-(D)Ser]⁸-Cyclosporine;
[O-acetyl-(D)Thr]⁸-Cyclosporine;
[Val]²-[O-acetyl-(D)Ser]⁸-Cyclosporine;
[Dihydro-MeBmt]¹-[Val]²-[O-acetyl-(D)Ser]⁸-Cyclosporine;
[Nva]²-[Nva]⁵-[O-acetyl-(D)Ser]⁸-Cyclosporine;
[Thr]²-[O-acetyl-(D)Ser]⁸-Cyclosporine; and
[Dihydro-MeBmt]¹-[Thr]²-[O-acetyl-(D)Ser]⁸-Cyclosporine.
5. A pharmaceutical composition useful in inducing immunosuppression or treating inflammation or parasitic infection comprising a cyclosporin as defined in claim 1 together with a pharmaceutically acceptable diluent or carrier therefor.
6. A method of inducing immunosuppression, of treating inflammation or of treating parasitic infection in a subject in need of such treatment, which method comprises administering to said subject an effective amount of a cyclosporin as defined in claim 1.

* * * * *